United States Patent [19]

Clark

[11] Patent Number: 4,831,527

[45] Date of Patent: May 16, 1989

[54] DYNAMIC MEASURING SYSTEM FOR DETERMINING THE AMOUNT OF EXCESS BODY FAT

[76] Inventor: Lloyd D. Clark, 15 Conrad St., San Francisco, Calif. 94131

[21] Appl. No.: 895,261

[22] Filed: Aug. 11, 1986

[51] Int. Cl.[4] .......................... A61B 5/10; G01H 7/00
[52] U.S. Cl. ................................ 364/413.02; 73/579; 128/774
[58] Field of Search ................ 73/79, 866.2, 579, 433, 73/580; 177/25.11, 25.12, 25.13; 128/774; 364/567, 415

[56] References Cited

U.S. PATENT DOCUMENTS

| | | | |
|---|---|---|---|
| 3,548,645 | 12/1970 | Sikorski et al. | 73/79 |
| 3,555,886 | 1/1971 | Thornton | 73/580 |
| 3,735,247 | 5/1973 | Harker | 324/226 |
| 4,008,405 | 2/1977 | Neumann | 307/231 |
| 4,050,530 | 1/1977 | Storace | 177/1 |
| 4,144,763 | 3/1979 | Vogelman | 73/433 |
| 4,184,371 | 1/1980 | Brachet | 73/433 |
| 4,347,903 | 9/1982 | Yano | 177/25 |
| 4,412,298 | 10/1983 | Feinland | 364/567 |
| 4,429,574 | 5/1984 | Barry | 73/580 |

FOREIGN PATENT DOCUMENTS

| | | | |
|---|---|---|---|
| 2533030 | 3/1984 | France | 128/774 |
| 0150573 | 11/1962 | U.S.S.R. | 128/774 |
| 2168489 | 6/1986 | United Kingdom | 128/774 |

OTHER PUBLICATIONS

Sarychev, V. A. et al. "Device for Mass Measurement Under Zero-Gravity Conditions", *Acta Astronautica*, vol. 7, No. 6, Jun. 1980, 719-730.
Brown, B. S. "Analysis of Body Composition", *J. Clin. Comput.*, vol. 14, No. 1, 1985, 1-10.

*Primary Examiner*—Clark A. Jablon
*Attorney, Agent, or Firm*—David Pressman

[57] ABSTRACT

The fat-to-lean ratio of tissue on a human subject is measured by the subject standing on a platform (100), raising his or her heels, then allowing his or her weight to fall onto the board near a transducer to produce a force. A sensor transmits a voltage signal to an analog-to-digital (A/D) converter. The subject's stomach (300), buttocks (310), and other flesh will continue moving in a downward direction (335) (below their rest position) after the skeleton has stopped moving. This results in a downward force on the board which is registered as a data peak (580) in a computer through the action of the sensor and the A/D converter. Tissue elasticity will cause the stomach and buttocks to then move upward (350), above their normal resting position. This will result in a lessening of the force and a corresponding minimum (590) in the output wave. The wave thus is a damped sinusoid which can be analyzed using various means to result in an "excess pendulous fatty tissue index" which is indicated by humanly sensible readout display.

16 Claims, 4 Drawing Sheets

$$SLOPE = \frac{MAX - MIN \times N.F.}{I_{MAX} - I_{MIN}}$$

DYNAMIC MEASURING SYSTEM FOR DETERMINING THE AMOUNT OF EXCESS BODY FATcl BACKGROUND

Field of Invention

This invention relates to a novel system for measuring body fat, particularly loosely-bound or concentrated body fat. This is the excess fatty tissue which, in human beings, is evidenced by an overall or localized palpable layer of fat which is loose to the feel. It is further evidenced by an enlargement of various parts of the body, such as the stomach, buttocks, legs, and arms.

BACKGROUND

Fat Measurements Are Valuable

A measurement of the amount of fat in a human's body can be valuable and useful for many reasons. First, fat measurements can be a valuable aid in monitoring body tone. Further, they provide a means for monitoring and indicating the progress of a weight-loss or exercise program. An indication of a quantitative progression can be very valuable psychologically to the exerciser or reducer as a means of encouraging continued participation. Still further, when a person embarks on an exercise program, he or she will usually gain weight by virtue of added muscle mass. Thus the person may erroneously believe he or she is becoming "fatter", when in fact the ratio of fat to lean body tissue is actually declining. Measurements of the ratio of fat to lean tissue will correct this misinformation.

Prior-Art Fat-To-Lean Measurement Techniques Left Much To Be Desired

The ratio of fat to lean tissue in an animal's or in an inanimate body of tissue (such as a piece of meat, for example) can be measured in a number of ways. In one way, the ratio is determined with the aid of direct weighing and volume-determining apparatus using any of several techniques.

In one weight-volume method, the tissues are subjected to electromagnetic radiation. The electrical impedance characteristic of pure lean tissue which contains minimal fat is measured and recorded. The properties of a pure sample of fat are also measured and recorded. Then the tissue of interest is studied using the same method. The relative amounts of lean tissue and fat contained in the sample are determined by interpolation of the data (e.g., electrical impedance) between the known properties for pure fat and pure lean tissue.

A second class of measurements involves the determination of the volume of the subject. Once this is known, the subject is weighed and its density calculated. Again, the ratio of fat to lean tissue is determined by interpolation of the data between the two known densities for pure fat and pure lean tissue.

Harker, in U.S. Pat. No. 3,735,247, 1973, employs an electronic system to measure the "fat-to-lean" ratio of tissue, either in vitro or in vivo. His apparatus consists of electronic circuitry which uses non-contact means to measure the resistivity and dielectric constant of the tissue. An oscillator applies an alternating current signal to a solenoidal coil. The electromagnetic field thus produced is coupled to the tissue of interest. Generally, this is done by placing the tissue or animal inside a coil of appropriate size. Harker's circuitry then measures the impedance change in the coil brought about by insertion of the animal into the coil. The complex impedance of the animal tissue thus measured can be expressed in terms of real and imaginary components using variables well understood by those familiar with alternating-current electronic circuitry. These components in turn are used to determine the resistivity and dielectric constant of the sample tissue. Knowing the impedance of fat and lean tissue, it is possible by interpolation to infer the intermediate, relative amounts of fat and lean tissues contained within the volume of the coil.

While Harker's system provides information about the relative amounts of fat and lean tissue in a subject, it has a number of practical disadvantages. First, the determination of the ratio of fat to lean tissue is indirect. Using Harker's method, this ratio is determined by interpolation of the data between two known values: one for lean tissue, and the other for fat. Errors in the measurement technique could arise from non-linearities in the relationship between the impedance and the fat-to-lean ratio. Further, it is possible that fat distributed uniformly throughout the tissue would yield a different reading than fat lumped together at one location, especially if that location were near one end of the solenoidal coil where the electromagnetic field is divergent. Further, the requirement that the subject be placed inside a solenoidal coil could require a coil of substantial size, e.g. in the study of tissue in a human being. Thus Harker's system would not be suitable for home use. Still further, errors could result if the subject moves while the impedance is being measured.

Vogelman, in U.S. Pat. No. 4,144,763, 1979, employs two chambers to determine the density of an animal or human being. The chambers are coupled together by a connecting pipe and valves. His method consists of pressurizing the first chamber above atmospheric pressure and measuring the pressure in this chamber. The object to be measured is placed in the second chamber, which can be maintained at atmospheric pressure. Both chambers are then sealed from the outside environment. A valve in the pipe connecting the first and second chambers is then opened and the equalized pressure of the two chambers is measured. Using Boyle's law, the initial and final pressures may be used to calculate the volume of the body within the second chamber. The subject is then weighed and its density determined. Further calculations using empirical equations are then used to determine the percentage of body fat in the measured object.

Vogelman's method, like Harker's, also suffers from the requirement that the chambers be sufficiently large to contain the subject. In the study of human beings, the chambers will of necessity be large and relatively expensive, especially since they must be sealed against air leaks. Further, temperature changes during the measurement cycle or a temperature gradient between the two chambers could result in a false reading.

Brachet, in U.S. Pat. No. 4,184,371, 1980, describes an apparatus for measuring the density of a body. Brachet's apparatus comprises two chambers: one to receive the body, the other an auxiliary chamber. A subsonic wave generator, typically operating at 5 Hz, applies subsonic pressure waves to both chambers. A differential manometer is connected between the chambers and means are provided for equalizing the subsonic pressures of the chambers. Measurement means are driven by the mechanism for equalizing the above-mentioned subsonic pressures. Finally a scale in the first chamber weighs the body.

Although the weight of the body is obtained directly, using an ordinary scale, the body's volume must be obtained using volumetric pressure variations between the chamber containing the body and the reference chamber. This is accomplished by zeroing the commutating, differential manometer and noting the readings of the measurement means coupled to the mechanism which equalizes the pressures between the two chambers. A set of equations is then employed to give the volume and, knowing the weight, the density of the body.

Brachet's apparatus shares one impracticality with Vogelman's and Harker's: the volume of the chamber required for human study, for example, is very large. Further, an animal subject is unlikely to stand still during a measurement. This adversely affects the weight determination by introducing errors into the measurement.

Prior-Art Mass Determination Fat Measurement Methods Also Have Drawbacks

Other related prior-art fat measurement methods include the determination of mass by various means.

Storace, in U.S. Pat. No. 4,050,530, 1977, teaches a method and an apparatus for weighing or determining the mass of an object. A first table is supported above a floor or fixed reference surface by piezoelectric crystals. When an appropriate electrical signal is applied to the piezoelectric crystals, the table will vibrate. A second table is supported above the first by a second set of piezoelectric crystals. The second set of crystals couples the two tables together mechanically. The second table contains a "pan" which holds the object to be weighed.

An oscillating voltage is applied to the first set of piezoelectric crystals, i.e., the ones which support the first table above the floor or reference surface. By virtue of the mechanical coupling, the second set of piezoelectric crystals will vibrate at the same frequency as the first set. The amplitude of the signal voltage output from the second set of crystals is a function of the mass and/or supported weight in the pan. In practice, the oscillating voltage obtained from the second set of piezoelectric crystals, i.e., those which support the pan, is rectified. Thus, a steady direct-current voltage is obtained which is representative of the mass or weight in the pan.

Barry et al., in U.S. Pat. No. 4,429,574, 1984, describe a system containing apparatus and circuitry for measuring the mass and weight of a sample. Their system employs an electromechanical mass-spring cell assembly. The cell applies an oscillatory motion to the subject whose mass or weight is to be determined. Electronics associated with the cell maintains a resonant frequency oscillation in the system consisting of the subject and the electromechanical assembly. The mechanical resonant frequency of the system is a function of the mass of the sample. The sample's mass and the acceleration due to gravity can be used to determine the sample's weight.

Storace and Barry both assume that the subject is a simple mass which moves as a unit. Both systems will be subject to error if the subject's mass is composed of two or more loosely connected parts. These parts and the connection between them will have one or more mechanical resonance frequencies of their own. A beat frequency will result from the mixing of multiple resonant frequencies. It is possible that the amplitude of the beat note will be great enough to completely obscure the mass reading obtained. Similarly, if the subject moves during a measurement, errors will be indicated.

Further, both of these methods rely on the application of a mechanical perturbation to the subject. This can be undesirable if the subject is sensitive to the vibrations necessary to produce a reading.

Disadvantages Of Prior-Art Fat Determination By Weighing Techniques

A number of weighing techniques are also employed as an adjunct to fat-determining measurements.

Neumann et al., in U.S. Pat. No. 4,008,405, 1977, is concerned with the prevention of weighing errors caused by motion of the mass being weighed. Electronic circuitry is employed to sense variation in the apparent weight over some time period. The readout of the electronic scale is blanked until the motion-induced variability in the apparent weight is reduced below a threshold value. When the measured weight reaches a steady value, the electronic scale's readout display is activated.

Yano et al., in U.S. Pat. No. 4,347,903, 1982, describe an electronic weighing balance which ascribes an average weight to a body which tends to move while it is being weighed. An analog signal representative of the apparent weight on the balance is converted to a digital representation of this signal using analog-to-digital converter in well-known fashion. The subject to be weighed is placed in the pan of the scale. The apparent weight of the subject is measured periodically. An algorithm is used which optimizes the timing of the taking and storing of samples of the subject's apparent weight in order to minimize error in the final result. These samples are then averaged to yield the subject's actual weight.

Feinland et al., in U.S. Pat. No. 4,412,298, 1983, teach a method for tracking creep and drift of a digital scale after a load has been placed on the scale's pan. Electronic means employing an analog signal derived from the weight in the pan, and an analog-to-digital converter are used to obtain a digital representation of the weight being measured. A microprocessor circuit is employed to store the continuously updated tare weight just prior to weighing. After a load is placed on the pan and the balance has come to equilibrium, the creep and drift are continuously monitored. The tare weight is adjusted for the creep and drift. The storing of the adjusted tare weight results in a constant net weight being obtained.

Neumann et al and Yano et al eliminate errors caused by motion of the subject. Feinland et al eliminate errors due to creep and drift caused by a heavy weight. These methods strive to perfect measurement of the weight of the subject under varying conditions. None of these methods directly addresses the measurement of fat v. lean tissue.

OBJECTS AND ADVANTAGES

Accordingly, one principal object of this invention is to provide a reliable, inexpensive means for determining relative amounts of body fat and lean tissue. Other objects are to measure the amount of fat without the need for large measurement systems, enclosed chambers, and separate weighing and volume determinations, without the need to determine total body density, and then interpolate this to give relative amounts of fat and lean tissue, to accordingly provide a more accurate fat determination system, to provide one which is inexpensive, portable, and which can be operated by an amateur, no sophistication on the part of the user being required.

A further object of this invention is to provide a simple measurement system which does not require restraint of the subject, as in a chamber, to provide a measurement system which operates quickly and conveniently, which does not apply a signal or disturbance to the subject, and which is practical to use frequently, on a daily basis if desired, to monitor relative amounts of body fat over time as one might do during a diet. A further object is to provide a measuring system which is inexpensive and which can be bought for use in the home, perhaps as an adjunct to the common bathroom scale.

Additional objects and advantages of my invention will become apparent from a consideration of the drawings and ensuing description thereof.

DRAWING REFERENCE NUMERALS

Figure 1:
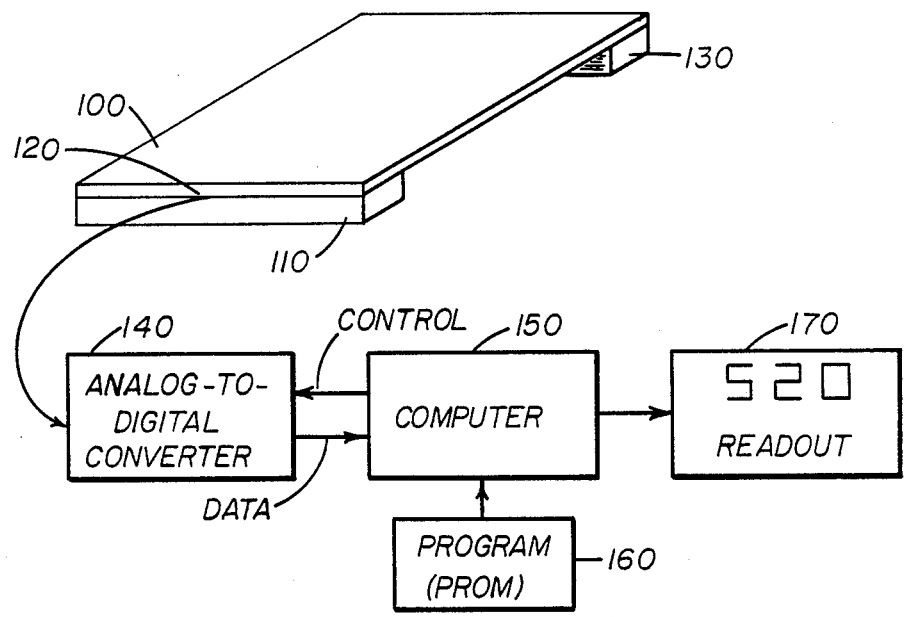
FIG. 1 shows a block diagram of an excess, loosely-bound fat measuring system according to the present invention.

100 Board
110 Foot
120 Sensor
130 Foot
140 Analog-to-digital converter
150 Computer
160 Programmable memory
170 Readout display
200 Rubber wafer
210 Relief hole
220 Force vector
230 Brass disc
240 Wire
250 Wire
300 Subject's stomach
310 Subject's buttocks
320 Directional arrow
330 Directional arrow
335 Directional arrow
340 Body's resting position outline
350 Directional arrow
500 Data plot
520 Data segment
530 Threshold value
540 Data segment
550 Data segment
560 Data segment
570 Data segment
575 Data segment
580 Data plot maximum
590 Data plot minimum
595 Slope
600 Data
610 Data
700 to 744 Program instructions

FIG. 1.—THE BASIC MEASURING SYSTEM

In the fat-proportion measuring system of the invention, an impulse force is applied to the body of a person, or body of tissue to be analyzed. A dynamic force-sensing apparatus is employed to provide a dynamic output voltage representative of the transient mechanical response of the body to this force. The force-sensing apparatus comprises a support means for supporting the subject mass of tissue, a transducer means which provides a dynamic output in response to the dynamic force exerted by the mass of tissue on the support, a dynamic output representative of the time-varying force exerted on the support, and conversion means for receiving and interpreting the dynamic output and providing an indication of the degree of damping in this output.

In use, the system causes the subject's body of tissue to move in one direction then abruptly stops motion in this first direction. After stoppage, the inertia of the tissue causes it to continue to move in the first direction. The elasticity of the tissue will cause some part of it to spring back and move in the opposite direction. Thus the resilience of the user's body causes oscillatory up-and-down motions of the body tissues in response to the impulsive force. These oscillatory motions are sensed by the transducer. The output of the transducer is indicative of the degree of damping. The degree of damping of this motion is inversely proportional to the proportion of concentrated, pendulous fat in the tissue. Thus the damping factor of these motions provides an indication of the subject's fat content.

The force-sensing apparatus comprises a simple board 100 (FIG. 1) and support 110 into which is inserted a transducer 120 which generates electrical signals in response to forces applied to the board. A similar support 130 is located at the other end of board 100 to render it level. Support 130 may also be thicker or thinner than support 110 in order to cause board 100 to slope upward or downward since a slight toe-to-heel tilt may be advantageous in some cases.

The above signal generated by transducer 120 is applied to the input of standard analog-to-digital converter (ADC) 140. The output of ADC 140 is a digital signal which is supplied to the input of a computer 150. Computer 150 is programmed by a suitable program 160 to perform data-taking and data-reduction algorithms. Thus the computer can interpret the electrical signal generated by the application of force to the apparatus. Once the data are interpreted by the computer, the result can be displayed in humanly-sensible form by readout display 170.

ADC 140 is preferably an 8-bit device such as type number AD670JN, manufactured by Analog Devices, Inc., Route 1, Industrial Park, P. O. Box 280, Norwood, Mass. 02062. Upon demand, this device will convert an analog input voltage to an 8-bit binary digital number representative of the magnitude of the voltage. ADC 140 has several data and control terminals which are connected to appropriate data and control lines on computer 150. Conversion is initiated by a command from computer 150. The conversion is complete within 10 microseconds, at which time the voltage-representative 8-bit binary number can be read by computer 150. The entire data-taking and reading sequence can be completed in a few tens of microseconds. This time is very short when compared to the rate of change of the data in this measurement. Hence the conversion time is insignificantly short and will cause no errors in the final voltage value measured.

Computer 150 is preferably any small microcomputer. The P8052AH-9035, manufactured by Intel Corporation, 3065 Bowers Avenue, Santa Clara, Calif. 95051 is one which is well suited to this application. Program 160 may be supplied to computer 150 in the form of a Programmed Read-Only Memory (PROM) chip (not shown) or by any other suitable, known method, such as by having computer 150 read a disk or other storage medium which contains the program. The program will be discussed below under FIG. 7.

Readout 170 may be any humanly-sensible numeric or alphanumeric display such as the HDSP-2300 manufactured by Hewlett-Packard, Inc., 640 Page Mill Road, Palo Alto, Calif. 94304.

FIG. 2.—THE FORCE SENSOR

Figure 2:
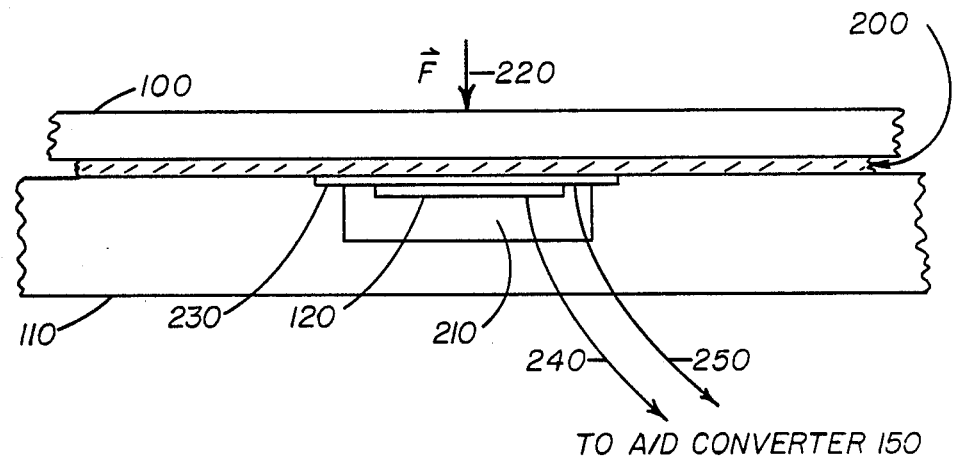
FIG. 2 is an enlargement of part of the platform of FIG. 1, showing in more detail the sensor portion of the system.

As shown in FIG. 2, a detailed cross-sectional view of the front side of board 100 and support 110, the top surface of board 100 is supported from beneath by slightly-compressible rubber wafer 200 and foot or support 110, into which a relief recess 210 has been formed. These construction features maximize the effect of applied force while preventing damage due to overbending of transducer 120.

An unknown bending force 220, such as that due to the deceleration or arrest of the subject's falling weight, is applied to board 100 and is measured by transducer 120, which comprises a piezoceramic element which generates a voltage in response to bending force 220. Piezoceramic element 120 is adhesively attached to the underside of a brass disc 230 which in turn is adhesively attached to support 110 at the edges of relief recess 210. Wire leads 240 and 250 are connected to the back and front sides respectively of piezoceramic element 120. (Wire 250 may alternatively be connected to brass disk 230 since the disk is intimately bonded to the back side of piezoelectric element 120.)

Although the sensor element in this case is a piezoelectric transducer of the type commonly found in audio output transducers, it could alternatively be any of a number of other strain-sensitive systems. An ordinary strain gauge with its commonly associated electronic circuitry would work as well. A piezoelectric element was chosen for its simplicity of installation and operation.

When force 220 is applied to board 100, the board bends slightly. Since piezoceramic element 120 is sandwiched beneath rubber piece 200, which is flexed by board 100, it also bends and thereby generates a voltage which is roughly proportional to the amount of bending of board 100. This signal is applied to ADC 140 (FIG. 1).

FIGS. 3a–3e. —THE MEASUREMENT PROCEDURE

The measurement procedure consists of a simple series of steps. The user stands on board 100 and causes a vertical impulsive force 220 from his or her body to be applied to board or platform 100. This transient force and all subsequent responses to it are sensed by sensor 120, read by ADC 140, recorded and interpreted by computer 150, and the result displayed by readout 170 under the control of the algorithm contained in PROM 160.

Figures 3A, 3B, 3C, 3D, 3E:
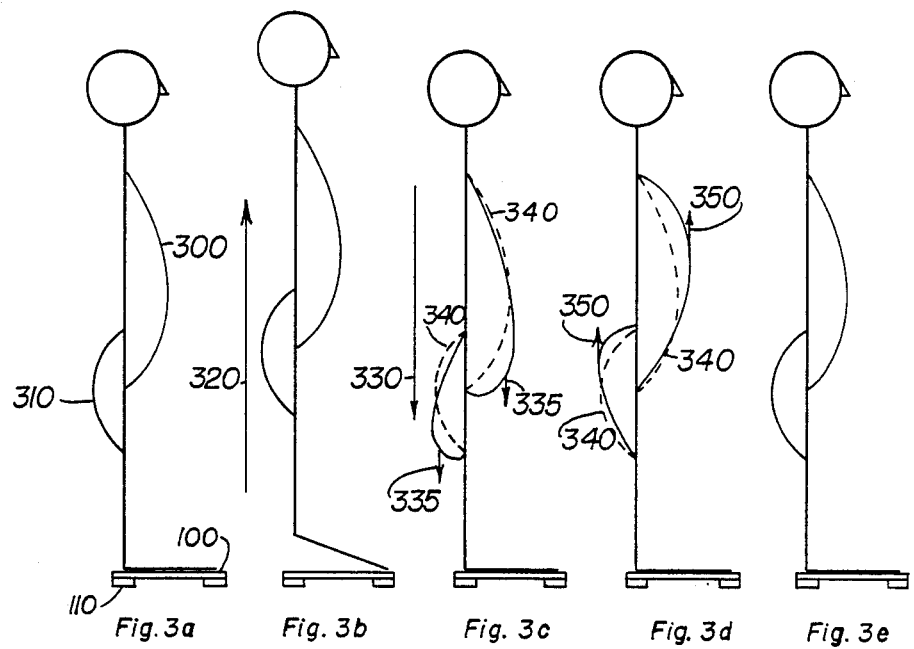
FIGS. 3a–3e are a schematic representation of the measurement procedure.

The subject whose excess, pendulous fat is to be measured may have any girth, weight, or fat distribution. As shown in FIG. 3a, the subject's body may have excess fat on stomach 300, buttocks 310, or elsewhere. To use the apparatus, the subject stands on board 100, as shown in FIG. 3a. The subject's heels are positioned above support 110, which as indicated in FIG. 2, contains sensor element 120. ADC 140 is continuously taking data at this point in time. Computer 150 is reading these data but not yet recording them. The body's resting position is shown by dotted lines 340.

As indicated in FIG. 3b by arrow 320, the subject then lifts up his or her heels a small distance, approximately 25 mm (1-inch); the subject does this by tightening his or her calf muscles in normal fashion. ADC 140 and computer 150 are still taking and noting data from sensor 120, but not recording them. At this point, experiment has shown that the most reliable measurements will be obtained if the subject tenses all his skeletal muscles as much as possible. This acts to separate the motion of the musculo-skeletal system from the excess, loosely-bound, pendulous, or concentrated fat, i.e., that fat which is not distributed throughout muscle, as is the fat in "marbled" meat. This facilitates measurement of the fat-to-lean ratio using this method. Further, it is proper for the subject to remove any shoes during this measurement since spongy heels will absorb some of the desirable impulse applied to the body by this measurement technique. For the same reason, it is best if the apparatus is placed on a hard surface during the measurement, preferably concrete or a wooden floor.

Next, as shown in FIG. 3c at 330, the subject releases the tightened calf muscles abruptly, allowing his or her weight to fall onto his or her heels, and thus heavily onto board 100. This shock produces a distinctive output from sensor 120 which is interpreted by computer 150 as a signal to begin recording the data obtained from sensor 120. Computer 150 records this data about once every 1/500 second. As the subject's body falls downward (arrow 330), it carries the excess fat with it. When the subject's heels hit the surface of board 100, the downward travel of his or her skeleton and skeletal muscles effectively ceases abruptly. However the excess, segregated, concentrated fat on stomach 300, buttocks 310, and other locations (such as the arms, back, and legs) will continue to move downward (arrow 335) below its usual resting position, as indicated by the solid lines.

This "additional" movement, beyond rest position 340, will stretch the body's connective tissue, skin, muscles, etc. Because of the elasticity of this stretched tissue, it will then spring back and up, as indicated by arrows 350, even though the subject is standing still. It will pull up and cause the excess fat in the stomach and buttocks to move up as indicated in FIG. 3d, to above its rest position. This will again stretch the aforementioned tissues, but this time by pulling them in the opposite direction. This action will continue so that the excess fat will move up and and down in a damped, oscillatory fashion, causing force 220 to oscillate or alternate between upward and downward directions about an average value.

Figures 4A, 4B:
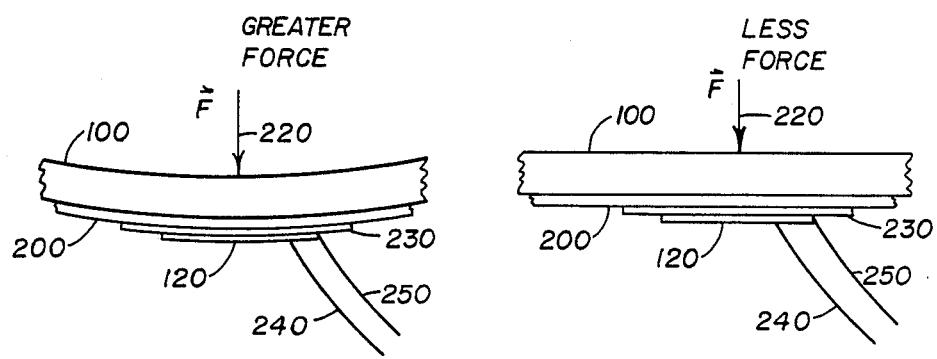
FIGS. 4a–4b are cross-sections of one preferred force sensor, a piezoelectric transducer element.

FIGS. 4a–4b. —THE SENSING ELEMENT

The oscillatory motion described above in connection with FIGS. 3 will cause sensor element 120, brass disc 230, rubber piece 140, and board 110 to flex down and up as shown (motion exaggerated) in FIGS. 4. It is well known that a voltage will be generated if a piezoelectric element is deformed as described here. This action causes a damped, oscillatory voltage, which is proportional to the amount of deflection of element 120, to be applied through connecting wires 240 and 250 to ADC 140 and stored in the memory of computer 150. Computer 150 stores data at predetermined intervals.

FIG. 5.—THE DATA OBTAINED FROM THE MEASUREMENT

Figure 5:
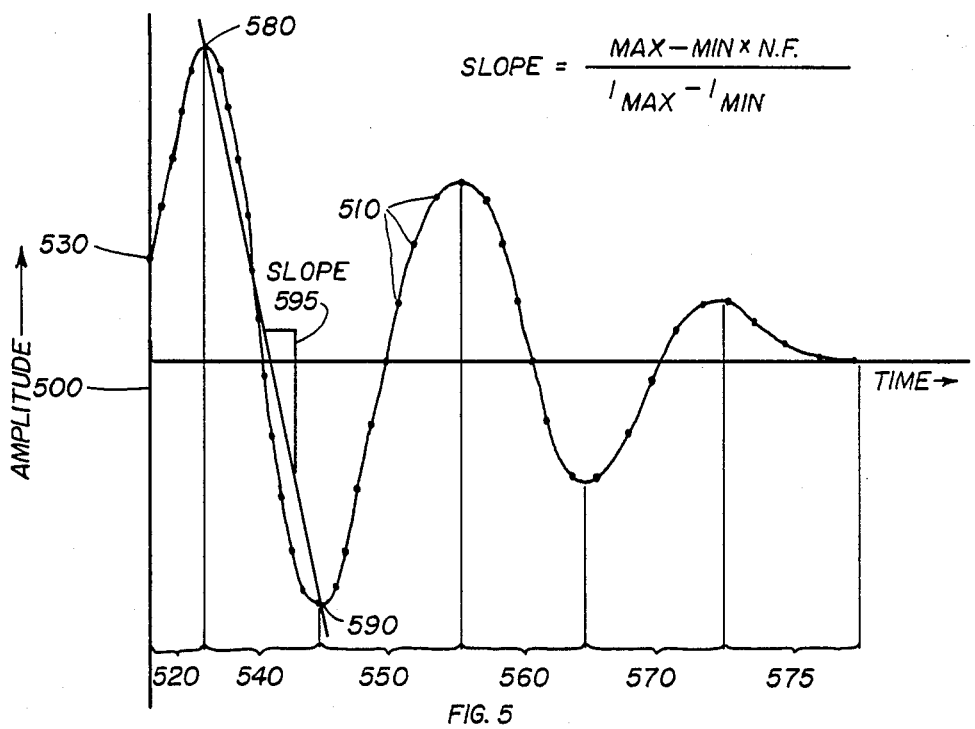
FIG. 5 is a plot of voltage output of the force sensor as a function of time.

FIG. 5 shows a typical plot 500 of amplitude v. time of the above-mentioned oscillatory voltage. This plot is formed by interconnecting samples 510 of the input voltage from sensor 120. Computer 150 has instructed ADC 140 to sample the analog input voltage at time intervals which are short compared to the duration of one cycle of the voltage wave obtained from sensor 120.

The downward motion 335 shown in FIG. 3c produces the first, or upward-going, part 520 of wave 500. Prior to the start of sampling, a part of the algorithm contained in the programming of computer 150 monitors the output of ADC 140. No data are taken until the amplitude exceeds a certain predetermined threshold 530. This threshold will be exceeded when the subject's weight drops onto board 100, thus initiating the body's transient oscillatory motion with a mechanical impulse.

Similarly, the subsequent oscillating motion of FIGS. 3d and 3e result in the downward-going part 540 and subsequent, damped parts 550, 560, 570, and 575 of the waveform. The measurement system composed of board 100, sensor 120, ADC 140, and computer 150 will take approximately 750 samples of the damped oscillatory waveform.

After the downward motion of the subject's body ceases, resilient forces provided by stretched skin, muscle, fat and connective tissue will cause an upward rebounding force, as explained above. This upward force is subtracted from the subject's apparent weight as sensed by sensor 120. The upward force is represented by segment 540 of data 500.

After a time, the upward motion of the subject's body tissues will cease, being forced downward again by the action of gravity and the somewhat less extended stretched skin, muscle, fat and connective tissue. The portion of wave 500 representative of this phase of the data are shown by data points in the next region, 550.

Similarly, there will be a slight overshoot again and the resultant upward motion of body tissues will produce yet another falling portion 560 of wave 500.

These oscillatory excursions will continue until all motion of the subject's body tissues has ceased. The damping of wave 500 is due to frictional forces arising within the subject's body tissues. The amplitude of wave 500 will finally decay to zero. The time elapsed during the measurable output of sensor 120 is typically 1.5 seconds. At that point, the data taking will cease and computer 150 will proceed to analyze the data. When the data analysis is complete, computer 150 will direct the results of its calculations to readout 170. Such results might be a single number which comprises a "excess, pendulous fat index".

FIG. 6.—ACTUAL DATA OBTAINED USING TWO DIFFERENT SUBJECTS

Figure 6:
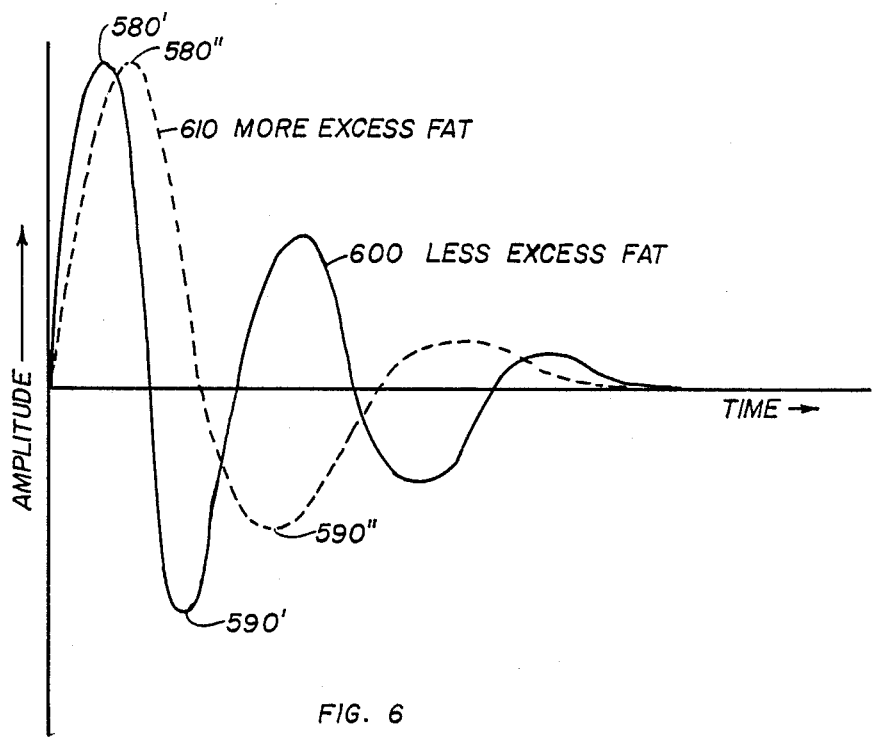
FIG. 6 shows the voltage output of the force sensor as a function of time for two different body types.

A comparison of oscillatory waves 600 and 610 from two different subjects, one fat and one lean, is shown in FIG. 6.

One of these subjects was a very thin male (180.3 cm tall, weighing 68.1 kg) with almost no excess body fat. When this subject lifted his heels and returned, as indicated in FIG. 3, transducer 120 produced wave 600.

The other subject was a husky male with more excess body fat (185.4 cm tall, weighing 79.4 kg). When this subject lifted his heels and returned, transducer 120 produced wave 610.

The difference between waves 600 and 610 is striking. The thin subject (wave 600) exhibits a much higher "mechanical ringing frequency" of vertical motion, characteristic of a very highly damped, low-mass mechanical system. The husky subject exhibits a much lower oscillatory frequency (wave 610), characteristic of a higher-mass, less-damped mechanical system. These motions can be analyzed using a mass, spring, and dashpot analogy, familiar to most students of engineering. The analysis of these motions can produce an "excess, pendulous fat index" which can be usefully indicated by readout display 170 (FIG. 1).

One simple index can be obtained by merely noting the slope of the line connecting the first maximum 580 and the first minimum 590 of the output waveform (FIG. 5). Results obtained from this simple measurement of three different male subjects having progressively increasing fat contents are given in Table I below.

These data were obtained using the following experimental protocol:
 1. The subject stands on platform 100.
 2. The subject raises his or her heels about 2.54 cm (one inch) above platform 100.
 3. The subject tenses all his or her skeletal muscles.
 4. The subject then abruptly relaxes the muscles in his or her feet and calves and lets his all his weight fall as rapidly and firmly as possible onto his or her heels, while keeping the skeletal muscles taut.
 5. The subject remains taut for approximately one second while the data obtained through the flexing of sensor 120 via the motion of platform 100 due to force 220 are being recorded.
 6. Computer 150 records the data and normalizes it so that the amplitude of first maximum 580 is the same for all subjects. This is done to remove differences in amplitude of the data caused by differences in weight of the subjects.
 7. Computer 150 then determines the slope 595 of the line joining first maximum 580 and first minimum 590 of the data. The results given in Table I are the averages of several readings.

TABLE I.

| Subject No. | Body Type | Slope |
|---|---|---|
| 1 | Endomorphic Male | 1.82 |
| 2 | Average Male | 3.23 |
| 3 | Ectomorphic Male | 5.25 |

The results shown in Table I justify the establishment of a "relative fat index". For example, a slope which lies in the range of 0–2 indicates that the subject is endomorphic, i.e. has very little fat. A slope in the range of 2–4 indicates an average subject. Slopes above 4 indicate an ectomorphic subject, i.e. one with excess body fat. Qualitative indicia with greater than these three levels can obviously be provided, e.g. "Very High Endomorph, High Endomorph, Medium Endomorph, Slight Endomorph, Normal," (etc.) would be a nine-level classification scheme.

FIG. 7.—FLOW-CHART EXAMPLE OF A DATA-REDUCTION ALGORITHM

Figure 7:
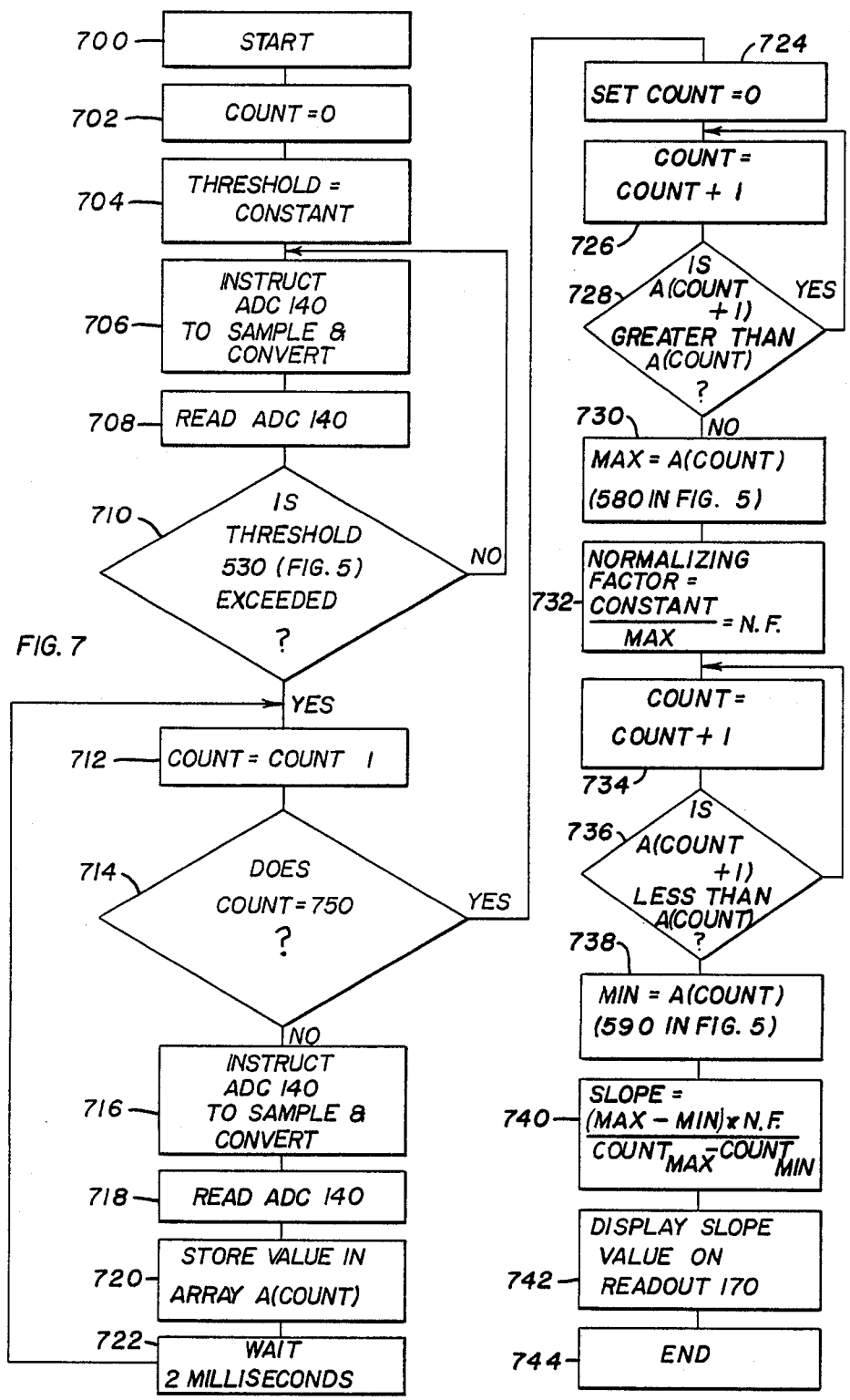
FIG. 7 is a flow chart of one algorithm which is used to provide an "excess pendulous fat index".

The flow chart in FIG. 7 can be implemented by any programmer by writing a computer program in any standard computer language, including Basic, Fortran, Pascal, "C", Forth, and assembly language. It will run on any programmable, generic computer. As indicated, it is represented in FIG. 1 by block 160, which may represent a PROM.

The program is initiated by the START command, block 700, at the top of the figure. Next, the computer sets an integer variable "COUNT" equal to zero. Another value "THRESHOLD", 704, is set to a constant value (530 in FIG. 5) which will be exceeded when the subject weight first falls onto board 100 above sensor 120.

Then computer 150 sends a signal to ADC 140, block 706, instructing it to sample the analog voltage present at the output of sensor 120, and then convert it to an 8-bit binary number representative of the amplitude of wave 500 and readable by computer 150.

Computer 150 then reads this number, block 708. If the THRESHOLD is not exceeded, 710, then computer 150 will repeat the sample-convert-read sequence and check again to see if the THRESHOLD value has been exceeded.

This process will continue until the THRESHOLD is exceeded, block 710. When the THRESHOLD is exceeded, the counting variable COUNT is incremented by 1, block 712. Since only 750 data points are required for this measurement, the computer checks to see if the value COUNT has reached 750, block 714. If not, another sample-convert-read sequence is performed, block 716, the value obtained is stored in an array A(COUNT), 720, the computer waits 2 milliseconds, block 722, then increments COUNT, block 712, and repeats this process until 750 data points are stored in the computer's memory.

Next, the stored data are analyzed. The value COUNT is again set equal to zero, block 724. It is then incremented by 1, block 726, and the data contained in the array A(COUNT) are examined, block 728. A(COUNT+1) is compared with A(COUNT).

If A(COUNT+1) is greater than A(COUNT), peak 580 (FIG. 5) has not yet been reached. This procedure is repeated until peak 580 is reached.

At this point, A(COUNT+1) will be equal to or less than A(COUNT). The value of this data point is stored as the variable MAX, block 730.

Next, a normalizing factor, N.F., is determined, block 732. N.F. is determined by a combination of the dynamic range of sensor 120 and ADC 140.

Next, COUNT is incremented, block 734, and A(COUNT+1) is compared with A(COUNT), block 736, until minimum 590 (FIG. 5) is detected. Minimum 590 is assigned the value MIN, block 738.

Next, slope 595 (FIG. 5) is determined, block 740, by the equation:

$$\text{SLOPE} = \frac{(\text{MAX} - \text{MIN}) \times N.F.}{(\text{COUNT MAX} - \text{COUNT MIN})} \quad (1)$$

COUNT MAX and COUNT MIN are the COUNT indices of variable A at the maximum 580 and minimum 590 of data 500, respectively. This slope value, representative of the excess, pendulous fatty tissue on the subject is then finally presented, block 742, to humanly-sensible readout display 170. This is the end, block 744, of the measurement. The program stops at this point. It may be re-initiated by another START command, block 700.

INTERPRETATION OF DATA

Slope 595 of wave 500 (FIG. 5) and waves 600 and 610 (FIG. 6) is one possible index of the amount of excess, pendulous fatty tissue. The algorithm of (FIG. 7) employed by computer 150 first normalizes the data so that peak 580 of wave 500 will be the same amplitude for all subjects. This normalization minimizes the effect of weight differences among subjects when determining the amount of excess, pendulous fatty tissue on a subject. Next, computer 150 begins a process which monitors the value of each succeeding sample 510 of wave 500. When the computer detects the fact that wave 500 is no longer falling, but has a point of inflection 590, the amplitude of wave 500 at point 590 is noted. The time which has passed between the detection of peaks 580 and 590 is noted indirectly by the two indices COUNT associated with the values MAX and MIN. From these four numbers, and the normalizing factor, N.F., a slope 595 of the data is be calculated as in formula (1) above.

Assuming a similar spring constant among subjects for the combination of skin, muscle, fat, and connective tissues, it is seen that the slope of wave 500 as determined above will vary as the amount of excess, pendulous fat varies among subjects. Wave 500 produced by the action of a very thin subject with little or no excess fat will have a very short duration between inflection points 580 and 590. This results in a relatively greater value for slope 595. In the subject with a large amount of excess fat, the frequency of oscillation of the system comprising the subject's body will be substantially lower, resulting in a longer duration of the upward portion 520 and the downward portion 540 of wave 500. This results in a relatively lesser value for slope 595.

SUMMARY, RAMIFICATIONS AND SCOPE

It is thus seen that the present invention provides a simple, inexpensive measurement system for determining the fat-to-lean ratio in human beings and is superior to prior art methods for measuring the fat-to-lean ratio of tissue. This is especially true for the measurement of apparent, excess, loosely-bound, segregated or concentrated fat, such as that occurring in the case of obesity. No large chambers or coils are required to contain the sample subject. The measurement can be performed by an amateur. Further, the measurement is of such short duration that it can be performed frequently, if desired. Further, the measurement device is portable, about the size of a bathroom scale. In fact, with minor adjustments, the measurement device can be incorporated into an ordinary bathroom scale. Such a scale would provide two kinds of data: (1) fat-to-lean index, and (2) weight, the latter being useful to human subjects who wish to watch their weight. Yet another advantage of the present invention is the fact that no electrical signals or mechanical disturbances are applied to the subject. The subject provides his own motive force for the experiment. This eliminates any risk of injury to the subject. Further, the forces applied by the subject in the present invention are approximately the same as those encountered during walking.

While the above description contains many specificities, these should not be considered limitations on the scope of the invention, but rather as an exemplification of one presently preferred embodiment thereof. Many other ramifications are possible.

For example, piezoceramic element 120 could be replaced by an ordinary strain gauge and its associated electronics. In an alternative embodiment, an analog computer could be used in place of the digital computer system of FIG. 1 and the algorithm of FIG. 7. Analog circuitry could sense the changes of slope associated with points 580 and 590 (FIG. 5). The voltage amplitude values of wave 500 could be sampled, normalized, and interpreted, all by analog circuit means.

Further, instead of requiring the user to raise his or her heels, a rocking board could be employed in addition to the fixed board (100 of FIG. 1). In this case, a pivot such as a dowel, perhaps one centimeter (approximately ½") in diameter would be placed on top of and near the center of board 100. The dowel would be oriented in such a fashion that a second board placed upon it would lift the user's heels as described above in connection with FIGS. 3. Such a system would provide a bistable board mechanism which could render it simpler for some users to operate the system.

An alternative to the above pivoting arrangement would be to use the system shown in FIG. 1 and to place a larger dowel underneath board 100. The diameter of the dowel would be greater than the height of feet 110 and 130. Board 100 would then be able to rock back-and-forth using the dowel as a pivot. In this embodiment, the bistable rocking feature would not require a second board.

Yet another variation of my fundamental design would be an all-mechanical system. In this case, the electronics could be eliminated entirely. Sensor 120 would be replaced by a lever arrangement which operates a pen on a rotating drum, for example. The small positional variations associated with the up and down variations of force 220 would be translated into larger up-and-down motions of the pen. Data obtained in such a way would closely resemble the data shown in FIGS. 5 and 6. Data analysis would most likely be done manually. The procedure for the analysis of mechanically obtained data would be the same as that obtained by electronic means.

The term "damping", as used above and in the claims, refers to the speed of decay or attenuation of the motions and forces and consequent waveforms generated by the deceleration of the tissue being analyzed. While the damping has been measured by the slope of the second component of the waveform, any other method of analyzing the damping of the waveform can be substituted. For example, the height of the second positive-going peak could be compared with that of the first positive-going peak. The ratio of these two heights is indicative of the degree of damping in the subject's body tissues. Alternatively, the frequency of the output waveform could be used as an indication of the mass and spring constants in the system, which in turn can be related to the excess fat on a subject's body.

Further, rather than have the subject drop his or her weight onto the transducer-containing support surface, an impulsive force could be applied to the subject's body by a mechanism within the support surface. This impulsive force would act in the same way as the voluntary, dropping force. This would be useful in the case of animals which cannot be taught to drop their own weight onto the surface. Similarly, by employing the external force-application mechanism, the system of this invention can also be used to measure fat in other tissue, such as meat, to provide a useful indication for those who must reduce cholesterol or to grade meat for fat content.

Accordingly the scope of this invention should be determined not by the embodiments illustrated, but by the appended claims and their legal equivalents.

I claim:

1. A method for determining the amount of fat in a body of tissue containing leans and excess, concentrated fat, comprising:
   causing said body of tissue to move in one direction,
   stopping the motion of said body of tissue at a sufficient rate of deceleration so that, after stoppage, the inertia of said tissue causes at least part of it to continue to move in said one direction and then the elasticity of said tissue causes at least part of it to bounce back and move in the opposite direction, and
   sensing the force produced by the motion of said tissue in said one and then said opposite directions and providing an output indicative of the degree of damping, and hence the inverse of the proportion of fat, in said motions of said tissue,
   said sensing comprising providing a support arranged to support said body of tissue and providing a transducer which senses the degree of bending of said support in response to the motions of said body of tissue and provides an output corresponding to such bending.

2. The method of claim 1 wherein said sensing also comprises providing a computer responsive to the output of said transducer and programming said computer to provide an indication of the degree of damping in said output.

3. The method of claim 2 wherein said programming is arranged to cause said computer to provide an output indicative of the slope of a component in the waveform of the output of said transducer.

4. The method of claim 1 wherein said output is provided in a qualitative manner by means of a numerical indication.

5. The method of claim 1 wherein said output is provided in a qualitative manner by means of one of a plurality of descriptive indicia.

6. A dynamic fat determination system for providing an indication of the proportion of fat in a human body, or other mass of tissue, comprising:
   (a) support means for supporting said mass of tissue,
   (b) transducer means for providing, in response to any dynamic force exerted by said mass of tissue against said support means, a dynamic output representative of the temporal profile of the dynamic force exerted against said support, and
   (c) conversion means for receiving said dynamic output and providing an indication of the degree of damping in said dynamic output.

7. The dynamic fat determination system of claim 6 wherein said support means comprises a rigid platform.

8. The dynamic fat determination system of claim 7 wherein said rigid platform comprises a flat, rigid board and a plurality of supports at opposite ends of said board.

9. The dynamic fat determination system of claim 8 wherein said transducer means is mounted in one of said supports.

10. The dynamic fat determination system of claim 6 wherein said transducer means comprises a piezoelectric crystal having a plurality of electrical leads extending therefrom and connected to said conversion means.

11. The dynamic fat determination system of claim 6 wherein said support means comprises a rigid platform and said piezoelectric crystal is mechanically fastened to said platform such that any bending force applied to said platform from said mass of tissue will bend said crystal.

12. The dynamic fat determination system of claim 6 wherein said transducer means is arranged to provide an electrical output and said conversion means comprises an electronic circuit for converting said electrical output to a visible indication.

13. The dynamic fat determination system of claim 6 wherein said conversion means comprises a computer programmed to provide an output indicative of the slope of a wave component of said electrical output.

14. The dynamic fat determination system of claim 13 wherein said output is a numerical indication.

15. The dynamic fat determination system of claim 6 wherein said transducer means is arranged to provide an electrical output having a waveshape with a first component which progresses in one direction and a second component which progresses in the opposite direction, and wherein said computer is programmed to provide an output indicative of the slope of said second component.

16. The dynamic fat determination system of claim 15 wherein said output is a numerical indication.

* * * * *